United States Patent
Najarian et al.

(10) Patent No.: US 9,962,124 B2
(45) Date of Patent: May 8, 2018

(54) AUTOMATED ANALYSIS OF VASCULATURE IN CORONARY ANGIOGRAMS

(71) Applicant: THE REGENTS OF THE UNIVERSITY OF MICHIGAN, Ann Arbor, MI (US)

(72) Inventors: Kayvan Najarian, Northville, MI (US); Sayedmohammadreza Soroushmehr, Ann Arbor, MI (US); Kevin R. Ward, Superior Township, MI (US); Brahmajee K. Nallamothu, Ann Arbor, MI (US)

(73) Assignee: THE REGENTS OF THE UNIVERSITY OF MICHIGAN, Ann Arbor, MI (US)

(*) Notice: Subject to any disclaimer, the term of this patent is extended or adjusted under 35 U.S.C. 154(b) by 16 days.

(21) Appl. No.: 15/356,012

(22) Filed: Nov. 18, 2016

(65) Prior Publication Data
US 2017/0148158 A1 May 25, 2017

Related U.S. Application Data

(60) Provisional application No. 62/258,175, filed on Nov. 20, 2015.

(51) Int. Cl.
*G06K 9/00* (2006.01)
*A61B 5/00* (2006.01)
(Continued)

(52) U.S. Cl.
CPC ........ *A61B 5/7203* (2013.01); *A61B 5/02007* (2013.01); *A61B 6/504* (2013.01);
(Continued)

(58) Field of Classification Search
CPC .................... A61B 5/7203; G06T 2207/10116
See application file for complete search history.

(56) References Cited

U.S. PATENT DOCUMENTS

| 8,831,304 B2 | 9/2014 | Xu et al. |
| 2007/0031019 A1* | 2/2007 | Lesage ...................... G06T 7/60 |
| | | 382/131 |

(Continued)

FOREIGN PATENT DOCUMENTS

| EP | 2693401 A1 | 2/2014 |
| WO | WO-2014/162273 A1 | 10/2014 |

OTHER PUBLICATIONS

Adla et al (NPL "Multimodality Imaging of Carotid Stenosis", International Journal of Angiology vol. 24, Mar. 2015, hereafter referred to as Adla).*

(Continued)

*Primary Examiner* — Oneal R Mistry
(74) *Attorney, Agent, or Firm* — Marshall, Gerstein & Borun LLP (57) ABSTRACT

A system analyzes angiogram image data, including video data, in order to extract vasculature information. Advanced image processing and machine learning techniques are used in pre-processing, frame selection, and vasculature segmentation to remove classes of artifacts from angiogram videos, and specifically from frames selected as having a sufficient amount of image data. From segmentation, accurate vasculature diameters are calculated, and, in some examples, stenoses and/or the extent of stenosis is automatically determined and displayed.

5 Claims, 8 Drawing Sheets

(51) Int. Cl.
  *G06T 5/00* (2006.01)
  *A61B 5/02* (2006.01)
  *A61B 6/00* (2006.01)
  *G06T 7/11* (2017.01)
  *G06T 7/62* (2017.01)
(52) U.S. Cl.
  CPC ............ *A61B 6/5258* (2013.01); *G06T 5/002* (2013.01); *G06T 5/005* (2013.01); *G06T 7/11* (2017.01); *G06T 7/62* (2017.01); *A61B 2576/023* (2013.01); *G06T 2207/10016* (2013.01); *G06T 2207/10116* (2013.01); *G06T 2207/30101* (2013.01); *G06T 2207/30168* (2013.01)

(56) References Cited

U.S. PATENT DOCUMENTS

| | | | |
|---|---|---|---|
| 2010/0104160 A1* | 4/2010 | Lavi | G06T 19/00 382/131 |
| 2010/0296709 A1 | 11/2010 | Ostrovsky-Berman et al. | |
| 2011/0081057 A1* | 4/2011 | Zeng | G06T 7/0012 382/128 |
| 2015/0282777 A1* | 10/2015 | Compas | A61B 6/481 600/431 |

OTHER PUBLICATIONS

Abbasi et al., Curvature scale space image in shape similarity retrieval, Multimedia Systems, 7:467-76 (1999).
Antiga, Generalizing vesselness with respect to dimensionality and shape, Release 1.00 (Aug. 3, 2007).
Buades et al., A non-local algorithm for image denoising, IN: Computer Vision and Pattern Recognition, CVPR 2005, IEEE Computer Society Conference, vol. 2, pp. 60-65 (2005).
Cardiovascular Angiography Analysis System—CAAS, PIE Medical Imaging, Sectra, AB, downloaded from the Internet at: <https://www.sectra.com/medical/radiology_imaging/solutions/ris-pacs/add-ons/3rd_party_providers/pie_medical/index.html> (prior art).
Cerquerira et al., Standardized myocardial segmentation and nomenclature for tomographic imaging of the heart a statement for healthcare professionals from the cardiac imaging committee of the council on clinical cardiology of the American Heart Association, Circulation, 105(4):539-42 (2002).
Dijkstra, A note on two problems in connexion with graphs, Numerische Mathematik, 1:269-71 (1959).
Frangi et al., Multiscale vessel enhancement filtering, In: Wells et al. (eds.), Medical Image Computing and Computer-Assisted Interventation MICCAI98, Lecture Notes in Computer Science, vol. 1496, pp. 130-137, Springer Verlag, Berlin, Germany (1998).
Funka-Lea et al., Automatic heart isolation for CT coronary visualization using graph-cuts, 3rd IEEE International Symposium on Biomedical Imaging: Nano to Macro, pp. 614-617 (2006).
Gülsün et al., Robust vessel tree modeling, Medical Image Computing and Computer-Assisted Intervention—MICCAI 2008, pp. 602-611, Springer (2008).
Kelm et al., Detection, grading and classi_cation of coronary stenoses in computed tomography angiography, Medical Image Computing and Computer-Assisted Intervention—MICCAI 2011, pp. 25-32, Springer (2011).
Kirbas et al., Vessel extraction techniques and algorithms: a survey, Proceedings of Third IEEE Symposium on Bioinformatics and Bioengineering, pp. 238-245 (2003).
Lorigo et al., Curves: Curve evolution for vessel segmentation, Med. Image Anal., 593):195-206 (2001).
Nain et al., Vessel segmentation using a shape driven flow, Medical Image Computing and Computer-Assisted Intervention—MICCAI 2004, pp. 51-59, Springer (2004).
Nikolaou et al., MRI and CT in the diagnosis of coronary artery disease: indications and applications, Insights Imaging, 2(1):9-24 (2011).
Patton et al., Retinal image analysis: concepts, applications and potential, Progress in Retinal and Eye Research, 25(1):99-127 (2006).
Pham et al., Current methods in medical image segmentation, Annu. Rev. Biomed. Eng., 2:315-37 (2000).
Pizer et al., Adaptive histogram equalization and its variations, Computer Vision, Graphics, and Image Processing, 39:355-68 (1987).
Tomasello et al., Quantitative Coronary Angiography in the Interventional Cardiology, IN: Kirac (ed.), Advances in the Diagnosis of Coronary Atherosclerosis, InTech, pp. 255-273 (Nov. 2011).
Wesarg et al., Localizing calcifications in cardiac CT data sets using a new vessel segmentation approach, J. Digit. Imaging, 19(3):249-57 (2006).
What is Coronary Heart Disease, National Institutes of Health, National Heart, Lung, and Blood Institute (updated Jun. 22, 2016).

* cited by examiner

AUTOMATED ANALYSIS OF VASCULATURE IN CORONARY ANGIOGRAMS

CROSS REFERENCE TO RELATED APPLICATION

This application claims the benefit of U.S. Provisional Application No. 62/251,175, filed Nov. 20, 2015, entitled "Automated Analysis of Vasculature in Coronary Angiograms," which is hereby incorporated by reference in its entirety.

FIELD OF THE INVENTION

The invention generally relates to the fully automated detection of coronary vessels and their branches in angiograms and, more particularly, to the calculation of a diameter of such vessels, detection of stenosis and determination of the percent narrowing of stenosis.

BACKGROUND

The background description provided herein is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

One of the major causes of death worldwide is coronary artery disease, for which stent implantation is a common treatment. Current diagnosis of coronary artery disease relies on visual examination of angiograms by operators to identify significant stenoses in arteries. While operators rely on experience for such examination, ultimately they apply estimation and intuition to determine significant stenoses, which means intra- and inter-operator variability and frequent false diagnoses. Yet, accurate detection of stenosis (and the extent of stenosis) is crucial in patient diagnosis and treatment. False stenosis detection, for example, can lead to unnecessary usage of stents, placing a huge financial cost on the patient, potentially complicating the patient's heart condition further. On the other hand, failing to diagnosis severe stenoses in coronary vessels could lead to considerable health risks, such as myocardial infarction.

These limitations in existing approaches to stenosis detection are well-known. Even with the more popular techniques, such as quantitative coronary angiography (QCA) where errors are lessened, errors still occur, plus significant human input and resource costs are required. And while the advent of new imaging technologies has helped provide better resolution and quality of medical images, identifying stenosis and the extent of it are still imprecise processes in estimation, just estimations based on better image data.

The result is that there is a great need for an automated system to quantitatively analyze angiograms to determine the extent and location of stenosis in arteries and recommend a stent (or other appropriate therapies) only if needed.

SUMMARY OF THE INVENTION

The present invention provides systems and techniques to analyze angiogram image data, including video data, in order to extract vasculature information. Advanced image processing techniques and machine learning are used in pre-processing, frame selection, and vasculature segmentation. In pre-processing, i.e., processing before vessel analysis, artifacts may be automatically removed from video sequences. There are different kinds of artifacts in angiogram videos, making it a challenge to segment vessels accurately. Therefore, the present techniques may apply tailored algorithms to remove known classes of artifacts (e.g., stitches, pacemakers, heartbeat motion artifacts, camera movement artifacts, etc.) from angiogram videos, and only from frames selected as having a sufficient amount of information to make sure removal, and other image clean up, most effective.

The present techniques apply advanced digital image processing and machine learning methods after this pre-processing and frame selection, to segment vessels from the processed angiogram data. From the segmentation, the present techniques are able to more accurately calculate the diameter of each branch in the vasculatures.

In some embodiments, the techniques further include a decision support system that may aid cardiologists in diagnosing diseases using calculated quantitative parameters of the vasculatures. These diagnoses include identification of stenoses and the extent of stenoses. As a result, as we show, the present techniques reduce human estimation error by providing an automatically executing baseline determining, standardization system for measuring vessel characteristics and pathologies.

In accordance with an example, a method for analyzing medical video image data for a subject, the video image data being formed a set of frames of medical image data, the method comprises: obtaining the medical video image data and performing a pre-processing on the obtained medical video image data by performing on each frame of the video image data (i) a denoise filtering on the obtained medical video image data, (ii) a removal of a first set of features, and (iii) an image quality assessment indicating an amount of usable image data appears in the frame; automatically selecting a subset of the frames of medical image data by performing on each frame of the video image data, (i) a vessel segmentation, (ii) a histogram analysis after the vessel segmentation, and (iii) determining an amount of visible vasculature for each frame, and further identifying, based on the amount of visible vasculature for each frame, frames having a desired amount of visible vasculature as the subset of frames of medical image data; automatically removing artifacts from the subset of frames of medical image data using a shape characteristic machine learning engine trained using a set of artifact training data, wherein the shape characteristic machine learning engine applies a width profile analysis on identified features in the subset of frames to determine if any of the identified features are artifacts, in which case the artifacts are removed; automatically performing segmentation on the subset of frames with artifacts removed, wherein the segmentation comprises an extraction of the vasculature of each of the subset of frames; automatically performing a width profile analysis on one or more portions of the vasculature in each of the subset of frames to determine an amount of stenosis in the vasculature; and aggregating the width profile analyses for the subset of frames to determine of an overall stenosis for the subject.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment

DETAILED DESCRIPTION

The present techniques provide an automated system to analyze angioplasty and other images. Along with new image acquisition techniques that provide better resolution and quality, new image processing techniques help the physician perform accurate diagnosis.

Figure 1:
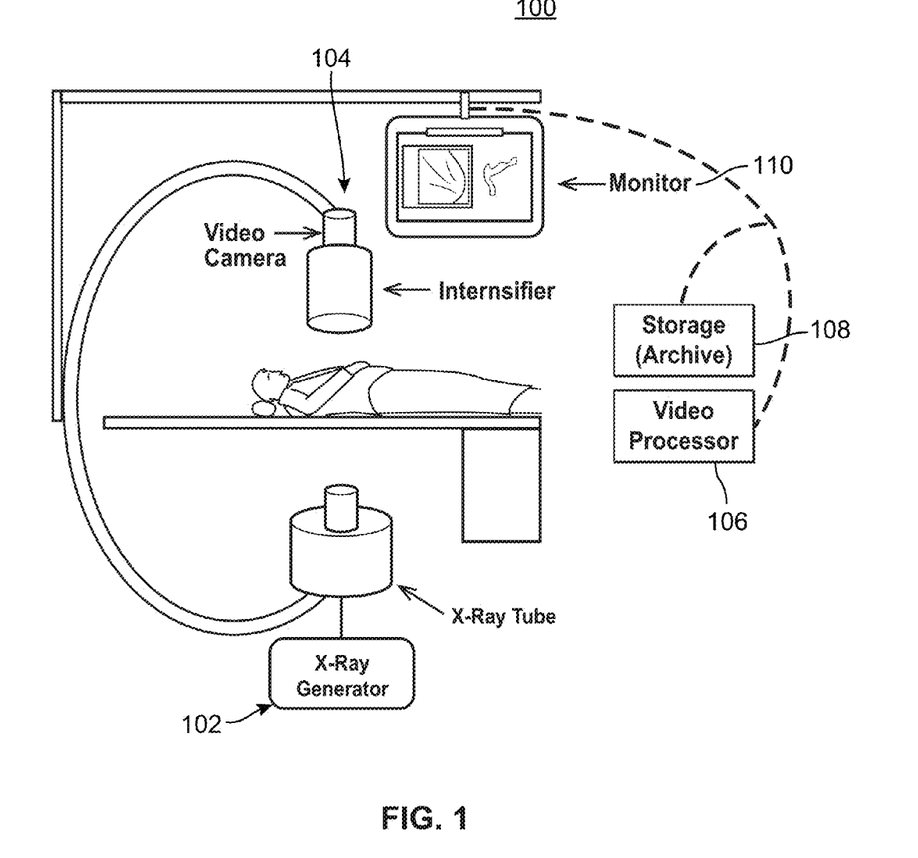
FIG. 1 illustrates an example X-ray angiography system in accordance with an example herein.

FIG. 1 illustrates a schematic diagram of an example of angiography system 100 having an X-ray source 102, an X-ray image detector 104, a digital video image processor 106, data recorder and storage 108, and display system 110 providing convention angiogram image collection and processing. While the examples herein are described in reference to an angiography system, the techniques may be applied to any number of medical imaging modalities and image types. Angiogram video data has been selected because of its standard use in stenosis detection.

The digital video image collected by the system 100 is provided to a quality assessment system 200 (FIG. 2) configured to examine the received image or video data, whether taken over a two-dimensional (2D) slice or over a three-dimensional (3D) volume.

Figure 2:
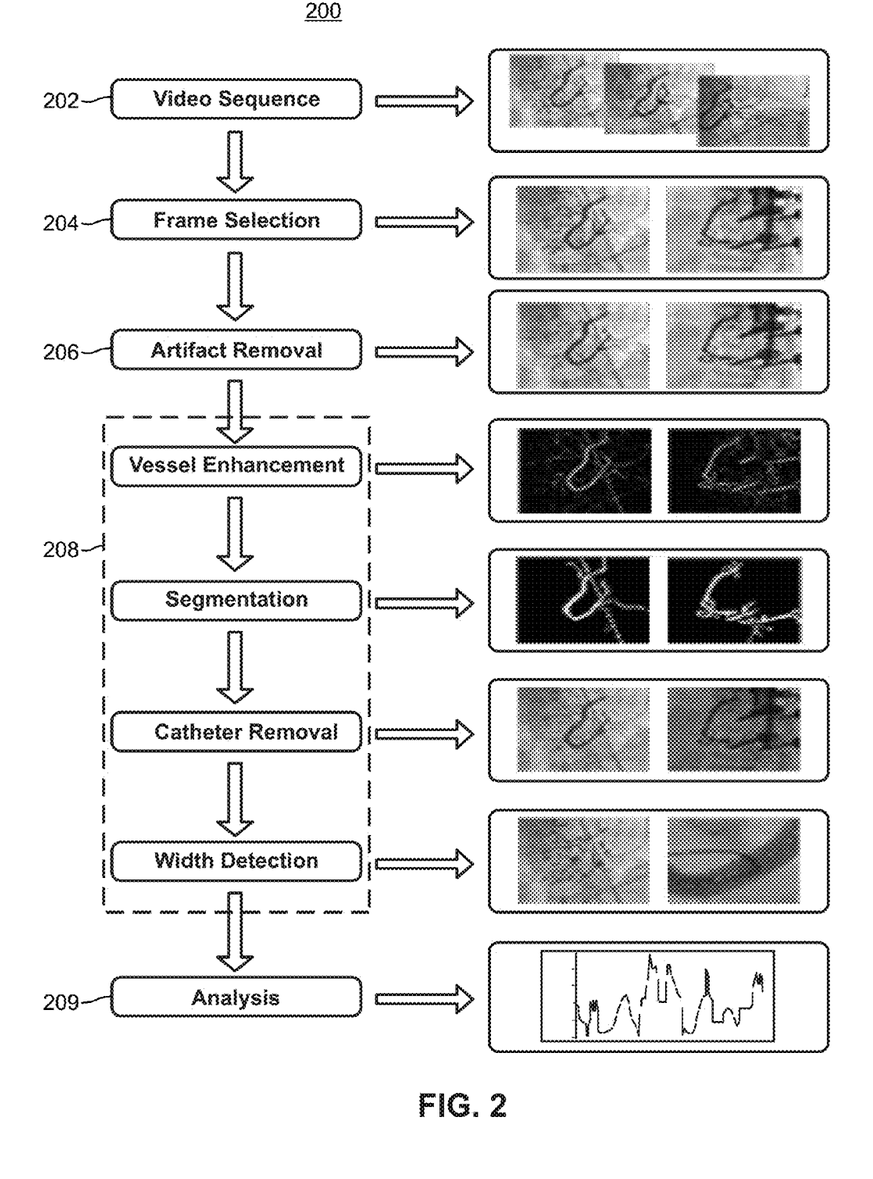
FIG. 2 illustrates a system for analyzing vasculature in angiography video data collected from the system of FIG. 1 or where the system is alternatively part of the system in FIG. 1.

The system 200, which is composed of various image processing and machine learning components each implemented using computer-readable instructions, stored in one or more memories and executed by one or more processes of the system 200, relies on a four-stage hierarchy that includes a pre-processing module 202, a salient frame module 204, an artifact removal module 206, a vasculature extraction module 208, and further include a quality assessment processing module 206. The modules, which are also described herein as "blocks" and "processes," may be implemented through these computer-readable instructions stored and executed by a system such as that shown FIG. 8 discussed below. Example implementations of each of these modules are provided below.

Pre-Processing

The pre-processing module (labeled video sequencer) 202 performs initial noise reduction, for example, using dedicated techniques as described herein below. Beyond conventional noise reduction, the pre-processing herein may include quality detection testing and data processing. This quality detection testing is linked, through processing, to the salient selection frame processes, to provide initial processing of all image frames forming the received angiogram video data. The pre-processing block performs initial quality assessment processing on each frame that allows the salient frame processes to identify and remove any frames in the video data that do have a sufficient amount of image from which an ultimate quality assessment may be determined. For example, the pre-processing block may apply a preliminary minimum threshold contrast determination on each image frame. Algorithm2: Denoising and Algorithm3: Vessel Enhancement show examples of pseudocode for the pre-processing steps.

More specifically, in some examples, the pre-processing module 202 performs a denoising process and contrast adjustment process, as follows.

Denoising: The pre-processing module 202 may take each frame of the video image and partition that frame into N×N non-overlapping blocks, after which in the pre-processing block a 2D Gaussian smoothing filter is convolved with each block to reduce the noise. An example 2D Gaussian filter would be:

$$G(x, y, \sigma) = \frac{1}{2\pi\sigma^2} \times e^{-\frac{x^2+y^2}{2\sigma^2}}$$

The parameter $\sigma$ is known as the kernel degree of smoothing diagram, which is adaptively calculated based on the standard deviation of the intensity for each block and for the whole image. This kernel parameter may be also calculated through training and by using machine learning methods.

Another denoising technique that can be used by the pre-processing module 202 is to apply a modified non-local means (NLM) technique, which replaces each pixel of an image with a weighted average of its closest pixels in terms of intensity value. In a NLM technique, a local pixel region (patch) around a pixel is compared to patches of pixels in the neighborhood of that pixel. The center pixels of the patches are averaged depending on the quadratic pixel distance between the patches. The discrete noisy image is given by $\{v(i)|v(i)\epsilon I\}$. At the averaging, an estimated value of each pixel is calculated which is the weighted average of all the corresponding pixels of the patches in its neighborhood. The resulting algorithm is shown in the following:

$$NL[v](i)\Sigma_{j\epsilon I}w(i,j)v(j)$$

where the family of weights depends on the similarity between pixels 'i' and 'j' and are normalized between 0 and 1. This similarity between two pixels 'i' and 'j' depends on the gray level intensity vectors $v(N_i)$ and $v(N_j)$ where $v(N_k)$ denotes a square neighborhood of fixed size centered at pixel 'k'. The similarity is measured as a decreasing function of the weighted Euclidean distance. Assuming Gaussian noise, the Euclidean distance is calculated as:

$$E\|v(N_i)-v(N_j)\|_{2,a}^2 = \|u(N_i)-u(N_j)\|_{2,a}^2 + 2\sigma^2$$

In the above equation u shows the image without noise. The pixels with a similar grey level neighborhood have larger weights in the average. The weights are defined here as:

$$w(i, j) = \frac{1}{Z(i)} \times e^{-\frac{\|v(N_i)-v(N_j)\|_{2,a}^2}{\sigma^2}}$$

where Z(i) is the normalization constant summing up every individual numerator over all neighborhoods. In this expression, in contrast to that above in the first denoising technique, the parameter 'σ' acts as a degree of filtering. It controls the decay of the exponential term and hence decides the decay of weights as a function of Euclidean distances. The patches involved in the above equations are selected spatially and also temporally. For the temporal patches, the corresponding pixels in the previous and next frames are considered and patches are selected.

In addition to denoising, the pre-processing module 202 may perform contrast adjustment. Because the background of the angiogram videos is not necessarily uniform, in order to improve the brightness differences across the dynamic range of the image uniformly the contrast adjustment may be used. For example, in an implementation, the pre-processing module implements a contrast-limited adaptive histogram equalization technique, which has the ability to enhance noise less than the original contrast enhancing methods. This technique works especially well on small patches in an image, and thus allows the system 200 to provide highly accurate frame selection, segmentation, and feature extraction for small vessel analyses and stenoses determination. The process examines the histogram of a patch and assigns a rank to the central pixel of the patch based on the pixel intensity in the calculated histogram. The resulted image is fed as the input image to the frame selection module 204. The process also reduces noise by partially reducing the local histogram equalization. In order to avoid block artifact bilinear interpolation is used.

Salient Frame Detection

The salient frame detection process 204 analyzes the received angiogram video frames and selects the preferred frames suitable for analyzing vessels. The salient frame detection may analyze each frame individually or in frame groups. The detection may determine which frames contain the most amount of information, which frames contain an insufficient amount of information to be exclude, which frames contain a sufficient amount of information, which minimum set of frames are needed to assure a desired level of quality assurance. Algorithm1: Salient Frame Selection shows an example of the pseudocode for frame selection steps.

In an example implementation, the salient frame detection module 204 applies an algorithm as follows. A filter processing is used to determine if geometrical structures in a frame can be treated as tubular, e.g., applying vessel segmentation techniques as discussed by Frangi et. al, Frangi, A. F., Niessen, W. J., Vincken, K. L., Viergever, M. A., Multiscale vessel enhancement filtering, Medical Image Computing and Computer-Assisted Interventation 98 (MICCAI98), pp. 130-137 (1998), incorporated herein by reference.

Figure 4:
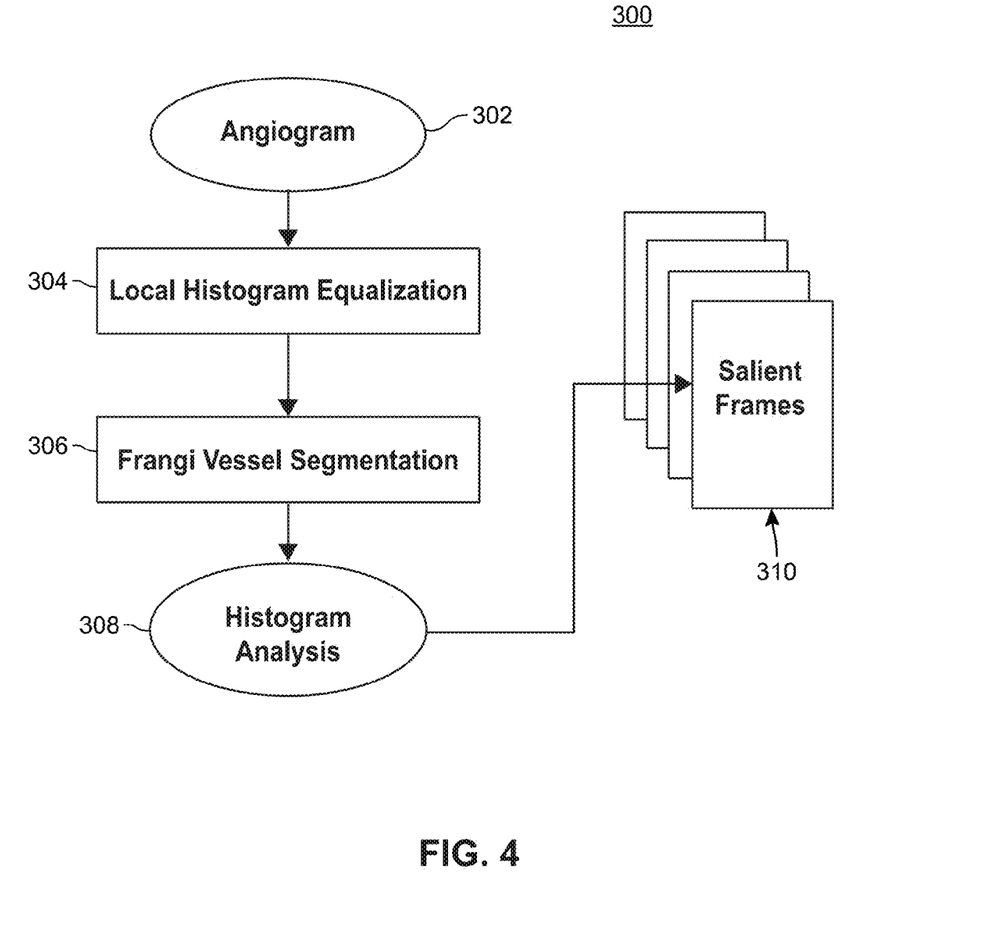
FIG. 4 illustrates a flow diagram of an example process for analyzing angiography data as may be implemented by the system of FIG. 2, in an example.

FIG. 4 illustrates an example implementation 300 of the frame detection module 204. Angiogram video data 302 is provided to a local histogram equalization process 304. The resulting video data is provided to a Frangi vessel segmentation process 306 that provides an input to a further histogram analysis process 308 that selects from all frames forming the video data, those frames 310 with the most salient information for further processing.

In an example, the filtering process analyses second order derivative information (i.e., Hessian). The second derivative of a Gaussian kernel at scale s measures the contrast between the regions inside and outside the range (−s,s) in the direction of the derivative. To identify salient frames, a spherical neighborhood at each point in a frame is mapped by the Hessian matrix at that point to an ellipsoid whose axes are along the directions given by the eigenvectors of the Hessian and the corresponding axis semi-lengths are the magnitudes of the respective eigenvalues. The process may use a 2D version of Frangi's method with the following equations:

$$V\sigma = \begin{cases} 0 & \lambda_2 < 0 \\ e^{-\frac{R_B^2}{2\beta^2}} \times \left(1 - e^{-\frac{S^2}{2c^2}}\right) & o \cdot w \end{cases}$$

where $V\sigma$ is a measure of vesselness at spatial scale σ. This is a matrix with the same size of the input image. Each entry of this matrix can be used as an indication of vesselness. In this equation, $S = \sqrt{\lambda_1^2 + \lambda_2^2}$ shows the Frobenius norm of the Hessian matrix where $\lambda_1$ and $\lambda_2$ are the eigenvalues of the Hessian matrix. S is also known as second-order structureness used to control the sensitivity of $V_\sigma$ to background noise. $R_B$ is a non-similarity measure defined as:

$$R_B = \lambda_1 / \lambda_2$$

$V\sigma$ is calculated with different values of σ and finally the maximum one is considered as the vesselness measure according to the following equation.

$$V = \max_{\sigma_{min} \leq \sigma \leq \sigma_{max}} V_\sigma$$

In these frames, a catheter artifact may also appear as part of the vasculature (higher intensity areas). Therefore, in some examples, the process uses a local histogram analysis to develop a metric representing the amount of vasculature contained inside the frame. This metric is determined for each frame.

The salient frame selection module 204 then selects the frames containing the maximum visible vasculature, without missing important information. In this way, the system recognizes that not all frames in video data contain useful information, or they may not contain a sufficient threshold of useful information, or they may contain an undesirable amount of questionable information (e.g., large amounts of potential artifact images that would make image processing a cumbersome and slow process).

For example, suppose that N is the total number of frames in an angiogram video, and $u_1', u_2', \ldots, u_N'$ are the denoised images and $V_1, V_2, \ldots, V_N$ are vesselness measures corresponding to the denoised images. The process selects two images from the $u_1', u_2', \ldots, u_{N/2}'$ and two from $u_{N/2+1}', \ldots, u_N'$ according to the following equations.

$$Max_1 = \underset{1 \leq r \leq \frac{N}{2}}{\operatorname{argmax}} \sum_i V_r(i)$$

$$Max_2 = \underset{1 \leq r \leq \frac{N}{2}, r \neq Max_1}{\operatorname{argmax}} \sum_i V_r(i)$$

$$Max_3 = \underset{\frac{N}{2} < r \leq N}{\operatorname{argmax}} \sum_i V_r(i)$$

$$Max_4 = \underset{\frac{N}{2} < r \leq N, r \neq Max_3}{\operatorname{argmax}} \sum_i V_r(i)$$

In these equations, $Max_1$ and $Max_2$ show the indices of the frames with the most visible vasculature from the first half of the angiogram video sequences and $Max_3$ and $Max_4$ are the indices of the frames from the second half of the angiogram videos with the most visible vasculature. The reasons that these frames were chosen in this way are described below, although other frame selection processes may be used.

In some cases it was observed that unintended artifacts (including catheters) biased the measure calculation, and this resulted in all the frames being chosen from a single small section of the video. Even though these were indeed frames representing good vasculature, the later part of the video showing a different part of the vasculature was not considered. This is owing to the movement of the camera during the angiography showing different parts of the vasculature. Therefore, in some examples, to compensate for overly weighted frame selection, a modification to the filtering algorithm was made, so that the frame selection was performed separately on two halves of the video frames making sure that all the parts of vasculature shown in the video were covered. Therefore, in some implementations the process chooses a first set of frames from the first half and of the frames and a second set of frames from the second half.

Artifacts Removal

The artifact removal process 206 includes computer-readable instructions for identifying different types of artifacts in angiogram videos. In particular, artifact removal is applied to the salient frames identified in the preceding process.

Artifacts may be removed sequentially. For example, the process 206 may predetermine that certain artifacts provide greater image distortion and should be removed before others. In an implementation, the process 206 removed three artifacts in order: stiches, catheter, and instruments. The process detected each sequentially by identifying the pixels corresponding to each artifact. The process then replaced these pixels with the average pixel intensity in pixels neighboring the artifacts pixels that were identified as not belonging to the artifact. Algorithm6: Artifact and Catheter Removing show examples of the pseudocodes for artifact and catheter removal step. For example, a catheter, with contrast dye injected into a vessel, can be an important source of artifact. In order to detect the catheter, the artifact removal process extracts statistical shape models and then identifies whether a pixel belongs to the artifact, using machine-learning methods such as Support Vector Machines, Random Forest, Deep Learning and Bayes Net. The machine-learning methods may be programmed with artifact specific features, which for a catheter examine includes the fact that a catheter might cross two borders of a frame. This feature along with other features such as shape characteristics is fed into a machine learning method that is trained using a set of training data.

In order to calculate the statistical parameters of a shape, the process 206 examined a rectangular patch around a pixel, and for each patch, edge information was extracted. A Hough transform was then applied to detect lines in the image. If the process determines that there is no line in a patch, then the process determines that there is no chance for the central pixel of the patch to be catheter. If it is determined that there is a line, then the process assigns a probability to the pixel, which shows how likely a pixel can be considered as an artifact.

In some examples, the artifact removal process 206 implements the following catheter detection protocol. Catheter curvature deviates little and is almost like a straight line. A curvature extraction process calculates the curvature defined as:

$$k(s) = \lim_{h \to 0} \frac{\phi}{h}$$

where $\phi$ is the angle between two tangent vectors, t(s) and t(s+h) where s is the arc length parameter. The following formula can be used to calculate the curvature function.

$$k(u) = \frac{\dot{x}(u)\ddot{y}(u) - \dot{y}(u)\ddot{x}(u)}{\sqrt{(\dot{x}(u)^2 + \dot{y}(u)^2)^3}}$$

In order to implement the curvature detection, a number of observatory assumptions were made. We noticed that a catheter runs across the image with its ends at the boundaries of the image. Further, compared to the vascular network, the catheter is significantly less convoluted, i.e., the tortuosity of the catheter is very less when compared to an end to end. Using an algorithm described by Dijkstra, E. W., A note on two problems in connexion with graphs, Numerische mathematic 1(1), 269-271 (1959), the shortest path between each set of boundary end points (not the case with both on the same boundary) is determined. The tortuosity for the path $P(v_i,v_j)=\{(v_i, v_i+1), (v_i+1, v_i+2) \ldots, (v_j-1, v_j)\}$ between $v_a$ and $v_b$ is calculated using:

$$\tau(v_i, v_j) = \frac{\sum_{t=i,(v_t,v_{t+1}) \in P(v_i,v_j)}^{j} f(v_t, v_{t+1})}{dist(v_i, v_j)}$$

In this equation, the ratio of the number of sequential points along that path (i.e., the sum of all the points in the edges comprising the path) to the distance between the end points of the path is calculated. The path with the highest relative tortuosity is identified to be the catheter and removed from the graph structure. The resulting skeleton image is free from catheters.

In a subsequent step, thin branches may be removed. For example, a vessel width-profiling algorithm may be executed as a preliminary filter to remove the branches having average width less than that of the catheter.

In this way, for one or more of the artifacts, a preliminary filtering may be performed before that artifact is identified for removal, to help ensure more accurate artifact removal.

Figure 5:
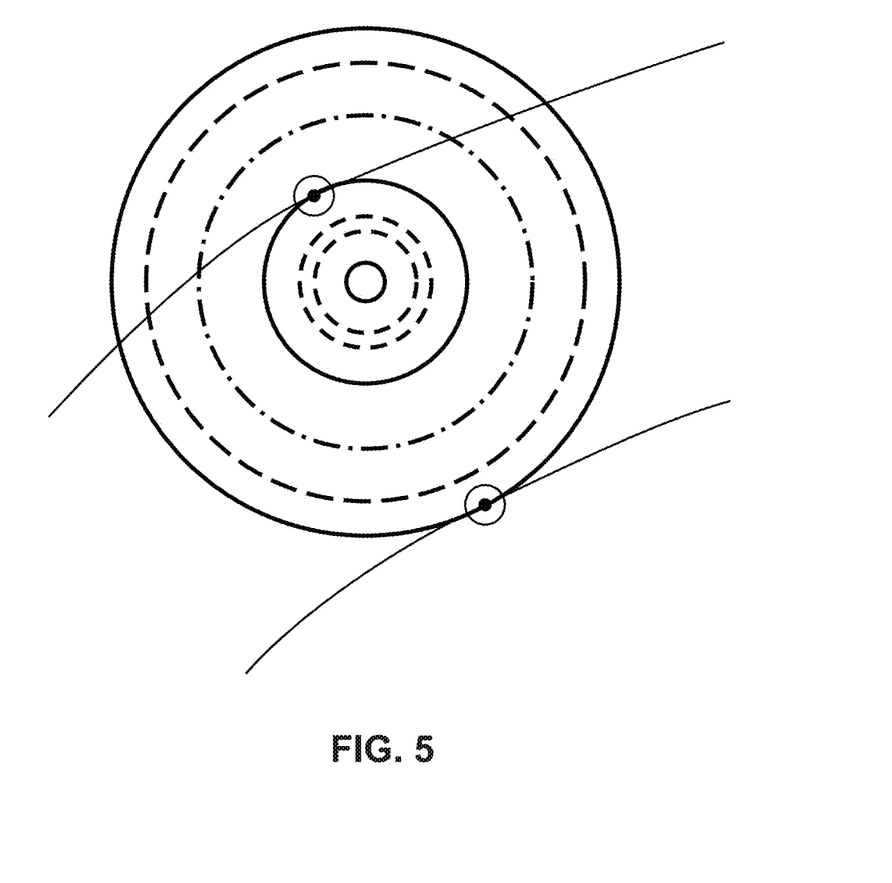
FIG. 5 illustrates cross-section analyses regions for a vessel analyzed in accordance with an example.

An example of width profile calculation is described in reference to FIG. 5. The center of the circles is on the skeleton of the network of arteries. In order to calculate the width of a vessel, a series of circles with different radii is plotted and those circles that are tangent to the boundary of vessels are selected and their radii are used to calculate the diameter of a vessel.

The process 206 may use machine learning to filter out the other artifacts, as well, while retaining vessel components from the segmentation. Region growing and thinning operations were employed in succession to obtain an accurate skeleton and branch-point network of the vascular structure visible in the frames. For each point in the edge map a window was defined and after performing a Local Histogram Equalization and Non Local Means smoothing, an edge map was created. Using this edge map, the process was able to estimate a profile of vessel thickness through an edge map derived in a local neighborhood around each point to determine the vessel thickness.

In any event, any such identified artifacts will be removed, in the order in which they were analyzed, from the particular salient frames identified by the process 204.

Vascular Extraction

After artifact removal, vessel enhancement, segmentation/extraction, catheter removal, and width detection occurs at the module 208.

The extraction module 208, for example, may determine the width of a vessel given an arbitrary point plying in the interior. The diameter of vessel shape objects or any curves in the image may be used as features in the process of artifact removal. There are two parameters involved in the algorithm: $\in$ and $n_d$. Let r represent the distance of any point from the point p. $\in$ represents the increment in r. $n_d$ represents the number of directions of exploration. These directions are further divided into two groups, the first group having directions making an angle from 0 to $\pi$ degrees from the horizontal, and the second from $\pi$ to $2\pi$ degrees. The first group is referenced as pertaining to the $\chi$ directions and the second as $\overline{\chi}$ directions. Also note here that the complimentary $\overline{\chi}$ direction to any $\chi$ direction is $\chi+\pi$ degrees. From the point p, the process may start exploring radially in the $\chi$ directions, incrementing r by at each stage until a boundary point is reached. For the $n_d/2$ first instances of boundary breach, the process records the value of r at each instance. Next, these steps are repeated fort directions recording again the first $n_d/2$ breaches of vessel boundary. The complimentary pairs (if they exist) of r corresponding to the directions obtained are summed and the minimum of those represent the width of the vessel at that point in that corresponding $\chi$-$\overline{\chi}$ direction pair.

To analyze the width profile, a Watershed segmentation was used to determine the profile associated with a blockage, and then to calculate the extent of stenosis. The percentage of stenosis is calculated as:

$$W = \left(1 - \frac{2d}{h_1 + h_2}\right) \times 100$$

where $h_1$ and $h_2$ are the peaks on either side of the trough and d is the depth of the trough. An example algorithm, Algorithm5 describes the details of width detection.

After the extraction module 208, the analysis module 209 analyzes the data to detect stenosis and the percent narrowing of stenosis.

Figure 6:
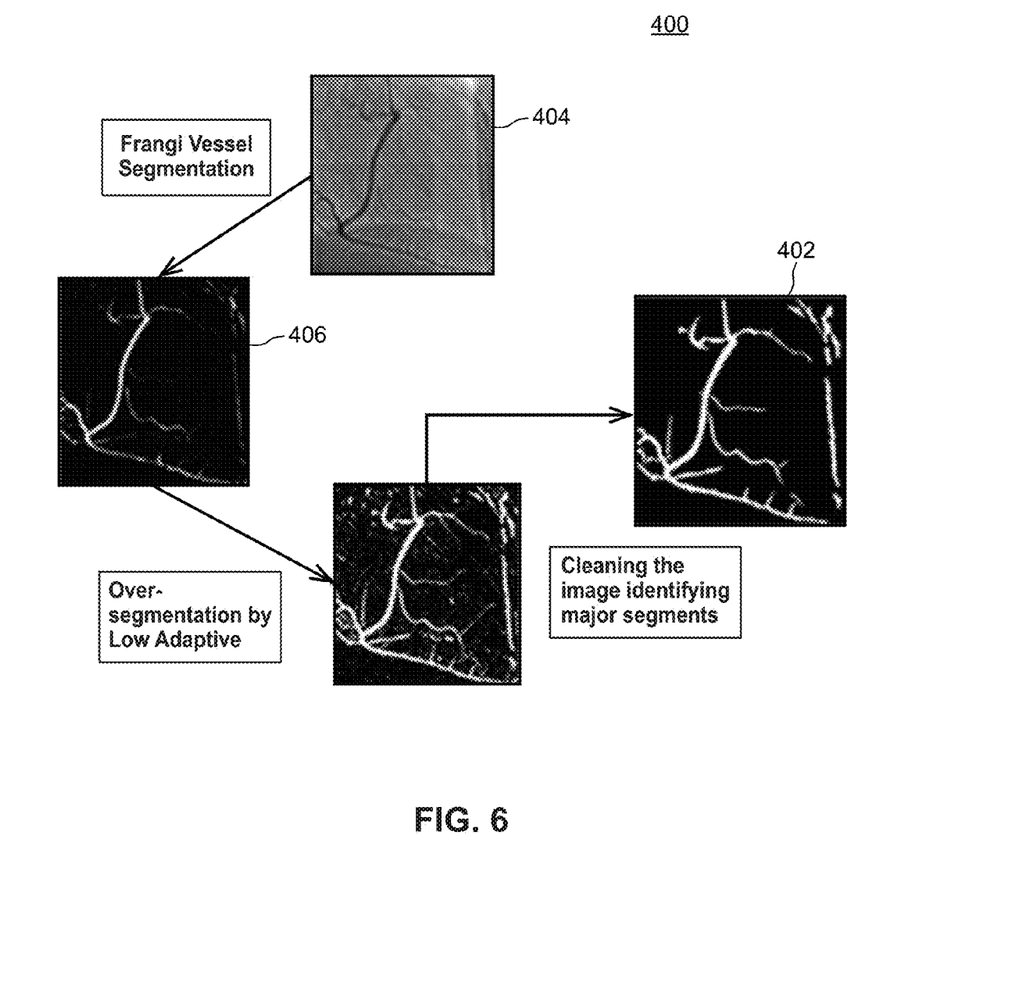
FIG. 6 illustrates a skeleton analysis of angiography data in accordance with an example.
Figure 7:
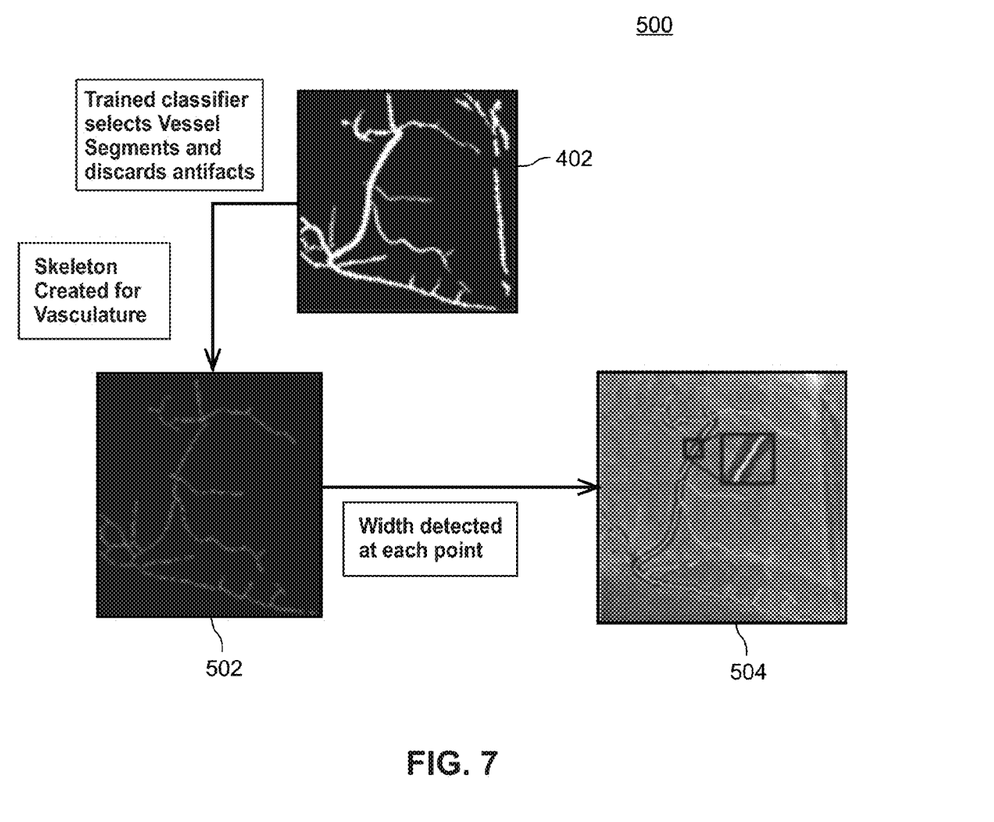
FIG. 7 illustrates a vessel profile analysis of angiography data in accordance with an example.

FIG. 6 illustrates an example implementation 400 of the present techniques segmenting a right coronary artery in received angiogram video data. FIG. 7 illustrates an example implementation 500 of a vessel profile analysis on the segmented right coronary artery image data from FIG. 6. The processes were based on 10 angiograms from a sample of patients undergoing coronary angiography. Patients with prior diagnosis of coronary artery disease, stent placement, or coronary artery bypass grafting were eliminated. In five (5) test cases, we compared (i) the results of a fully-automated system in accordance with the present teachings (ii) to an interpretation by a board-certified interventional cardiologist who annotated the images after traditional review. The result showed not only agreement between in the automated processes and the cardiologist, but a surprisingly greater amount of accuracy that went beyond the cardiologist's assessment. In the 5 coronary angiograms with annotation by a cardiologist, the algorithm was able to identify 48/56 lesions identified visually with 89% correlation between the percent diameter stenosis.

In FIG. 6, a Frangi vessel segmentation is performed resulting in the image transformation as shown. From there, an over-segmentation process is performed by an adaptive thresholding process resulting in the image with greater vasculature information as shown. From there, the resulting image is cleaned to identify major segments of the vasculature for vessel analysis and stenoses determination. As can be seen, image 402 contains higher contrast and great amounts of vasculature information than either original image 404 or segmented image 406. The process 400 may be performed on each salient frame.

In FIG. 7, vessel analysis 500 is performed on the segmented image 402. A trained classifier selects a vessel segment and discards artifacts identified in the image 402. The result is the creation of a vasculature extracted skeleton image 502. A width detection at various points along the vasculature is then performed to assess vasculature width profile and amount of a stenoses, as shown in image 504.

Figure 3:
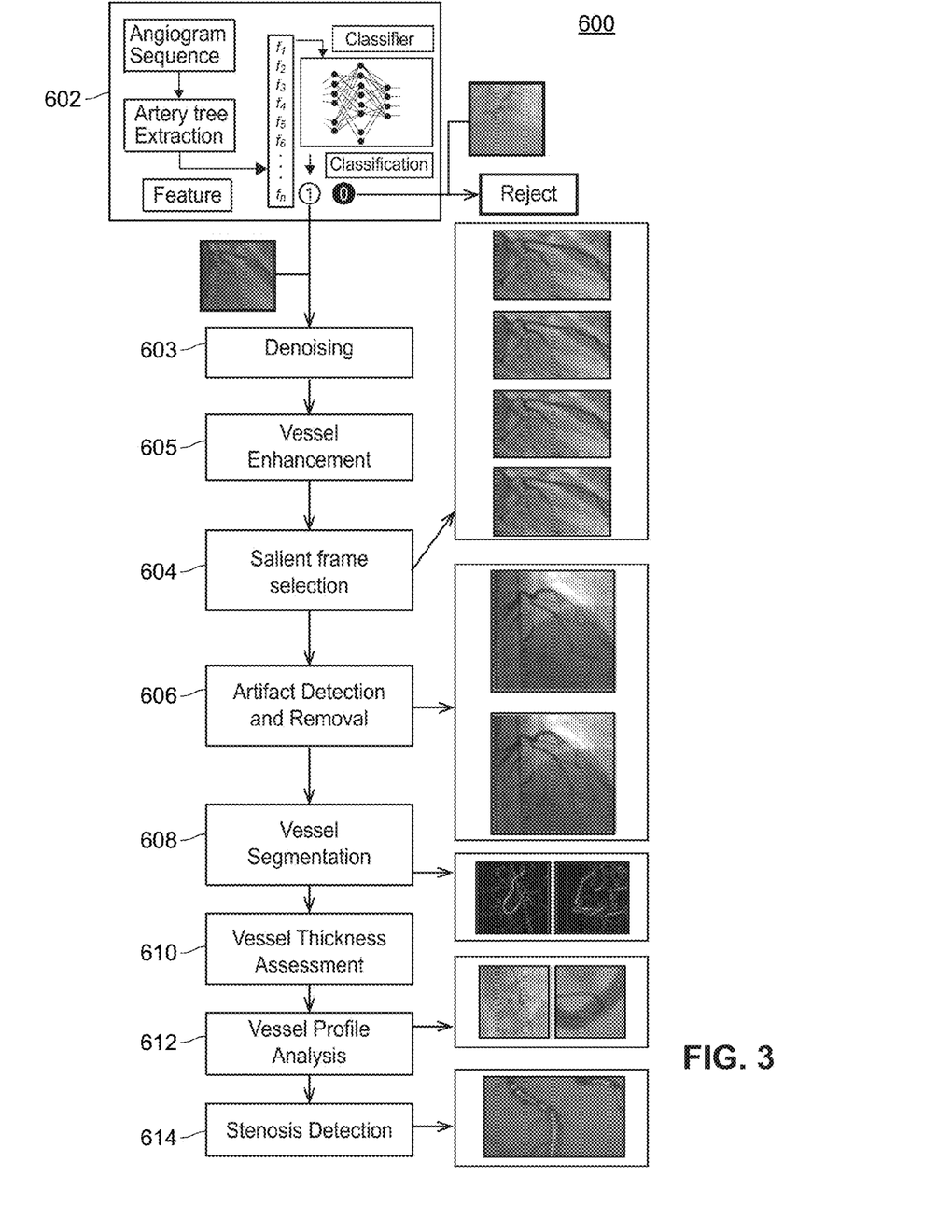
FIG. 3 is a detailed flow diagram of a process for analyzing angiography data as may be implemented by the system of FIG. 2, in an example.

FIG. 3 illustrates a more detailed process 600 for angiography video analysis and quality assessment, implementing the techniques described herein. An initial quality detection test is performed at a process 602 to perform a preliminary cut of image frames, identifying frames from which subsequent decision making would not produce statistically significant results. From this additional pre-processing is performed including denoising 603 and vessel enhancement 605. The remaining video frames are provided to a salient frames identification process 604 that identifies the most salient frames for further decisional analysis. The amount of frames identified at process 602 may be adjusted, by adjusted quality detection parameters, based on a predetermined image data load for subsequent processes. In other examples, the amount of pre-processing and filtering of processes 602, 603, and 605 may be adjusted continuously during operation of the process 600.

The salient frames are provided to a process 606 that finds regions within the frames corresponding to blood vessels and performs artifact detection and removal. The vessels are then segmented out of the image data at a process 608.

The thicknesses of one or more vessels is then determined by a process 610, and a process 612 then performs a vessel profile analysis that produces an amount of stenosis and percentage of stenosis 614 for each of the vessels analyzed. The stenosis assessment data may be provided to a quality assessment process that compares the normative assessment provided by the automated process of 602-614 to an external stenoses assessment made by a healthcare provider, e.g., to a prior human decision on stenoses made from examining the initial angiography data. The quality assessment process may then identify whether the human decision was accurate or not and provides a score of how far off the human decision was, i.e., the amount of actual stenosis in comparison to the estimated severity of stenoses identify by the human decision.

An example quality assessment process is provided below in example algorithm, Algorithm.

Algorithm: Angiogram classification
 1. Compute following feature for input angiogram video:
    F1=Number of frames in the video
 2. Compute following feature of each of four salient frame:
    F2=Number of branch point in the skeleton image
    F3=Ratio of number of arterial tree pixels over number of background pixels
    F4=Ratio of the number of branching points in the skeleton over the number of all skeletal points F5=Histogram of the average thickness of a coronary artery segment over all segments F6=Histogram of thickness variation within tabular region F7=Number of junction points with degree more than three F8=Histogram of number of curvature change points over the total number of skeletal points F9=Histogram of number of pixels in each segment F10=Histogram of lumen variation trough each segment 3. Apply a classifier (e.g. two layer neural network and decision tree) on this feature set as input 4. Compute the label accept or reject for each angiogram video as output of classifier.

Appendix A lists other example algorithms (labeled Algorithms 1-7) as may be implemental for various of the processes in FIG. 3.

Figure 8:
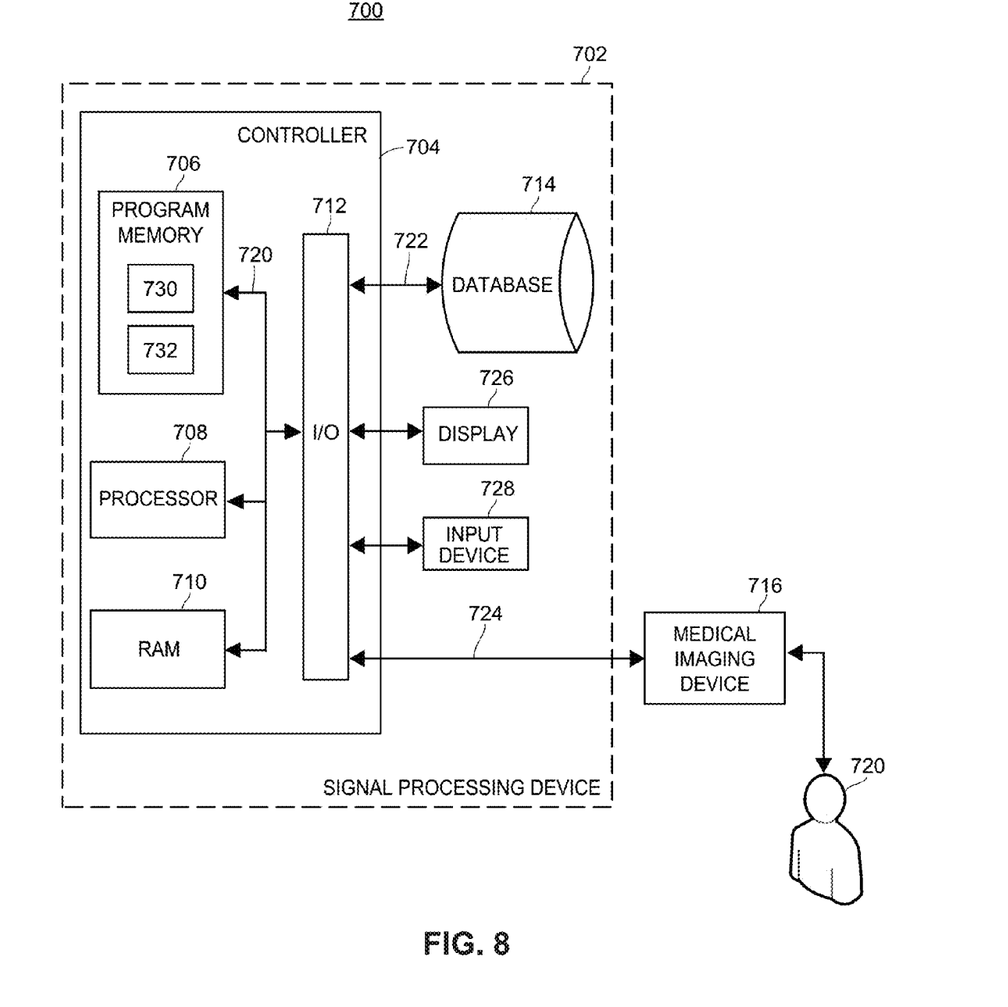
FIG. 8 is a block diagram of a schematic diagram of an example of decision support system, in accordance with an example.

In some examples, the system 200 may be executed on a computing system 700 as shown in FIG. 8.

FIG. 8 illustrates an example block diagram 700 illustrating the various components used in implementing an example embodiment of the present techniques. A signal-processing device 702 (or "signal processor" or "diagnostic device") is configured to collect angiography video data taken from a patient 720 via an imaging device 716 in accordance with executing the functions of the disclosed embodiments. The signal-processing device 702 may have a controller 704 operatively connected to a database 714 via a link 722 connected to an input/output (I/O) circuit 712. It should be noted that, while not shown, additional databases may be linked to the controller 704 in a known manner. The controller 704 includes a program memory 706, one or more processors 708 (may be called microcontrollers or a microprocessors), a random-access memory (RAM) 710, and the input/output (I/O) circuit 712, all of which are interconnected via an address/data bus 720. It should be appreciated that although only one processor 708 is shown, the controller 704 may include multiple microprocessors 708. Similarly, the memory of the controller 704 may include multiple RAMs 710 and multiple program memories 706. Although the I/O circuit 712 is shown as a single block, it should be appreciated that the I/O circuit 712 may include a number of different types of I/O circuits. The RAM(s) 710 and the program memories 706 may be implemented as semiconductor memories, magnetically readable memories, and/or optically readable memories, for example. A link 724, which may include one or more wired and/or wireless (Bluetooth, WLAN, etc.) connections, may operatively connect the controller 704 to the imaging device 716 through the I/O circuit 712. In other examples, the imaging device 716 may be part of the signal-processing device 702.

The program memory 706 and/or the RAM 710 may store various applications (i.e., machine readable instructions) for execution by the processor 708. For example, an operating system 730 may generally control the operation of the signal-processing device 702 and provide a user interface to the signal-processing device 702 to implement data processing operations. The program memory 706 and/or the RAM 710 may also store a variety of subroutines 732 for accessing specific functions of the signal-processing device 702. By way of example, and without limitation, the subroutines 732 may include, among other things: a subroutine for collecting video data from the imaging device 716, a subroutine for pre-processing that video data, a subroutine for determining salient frames from that video data, a subroutine for removing artifacts identified in those salient frames, a subroutine for performing vasculature extraction and vessel analysis, a subroutine for determining an amount of stenoses in vessels, and a subroutine for assessing the quality of the stenoses determination contained in stored medical assessment data, from third party assessments.

The subroutines 732 may also include other subroutines, for example, implementing software keyboard functionality, interfacing with other hardware in the signal processing device 702, etc. The program memory 706 and/or the RAM 710 may further store data related to the configuration and/or operation of the signal-processing device 702, and/or related to the operation of the one or more subroutines 732. For example, the data may be data gathered by the imaging device 716, data determined and/or calculated by the processor 708, etc. In addition to the controller 704, the signal-processing device 702 may include other hardware resources. The signal-processing device 702 may also include various types of input/output hardware such as a visual display 726 and input device(s) 728 (e.g., keypad, keyboard, etc.). In an embodiment, the display 726 is touch-sensitive, and may cooperate with a software keyboard routine as one of the software routines 732 to accept user input.

It may be advantageous for the signal-processing device 702 to communicate with a medical treatment device, medical data records storage device, or network (not shown) through any of a number of known networking devices and techniques (e.g., through a commuter network such as a hospital or clinic intranet, the Internet, etc.). For example, the signal-processing device may be connected to a medical records database, hospital management processing system, healthcare professional terminals (e.g., doctor stations, nurse stations), patient monitoring systems, automated drug delivery systems such as smart pumps, smart infusion systems, automated drug delivery systems, etc. Accordingly, the disclosed embodiments may be used as part of an automated closed loop system or as part of a decision assist system.

The system 700 may be implemented as computer-readable instructions stored on a single dedicated machine, for example, one with one or more computer processing units. In some examples, the dedicated machine performs only the functions described in the processes of FIG. 2, and any other functions needed to perform those processes. The dedicated machine may be a standalone machine or embedded within another computing machine, such as system 100. In other examples, the functions described in FIG. 2 are integrated within an existing computing machine, such as the machine 100.

In some examples, one or more of the functions of the system 700 may be performed remotely, including, for example, on a server connected to a medical imaging device (such as system 100), through a wired or wireless interface and network. Such distributed processing may include having all or a portion of the processing of system 700 performed on a remote server. In some embodiments, the techniques herein may be implemented as software-as-a-service (SaaS) with the computer-readable instructions to perform the method steps being stored on one or more the computer processing devices and communicating with one or more user devices, including but not limited to system 100.

Throughout this specification, plural instances may implement components, operations, or structures described as a single instance. Although individual operations of one or more methods are illustrated and described as separate operations, one or more of the individual operations may be performed concurrently or in an order other than the order illustrated, unless the context indicates otherwise. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, modules, or instructions. These may constitute either software (code embodied on a non-transitory, tangible machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware components of a computer system (e.g., a processor or a group of processors) may be configured by software (e.g., an application or application portion) as a hardware module that operates to perform certain operations as described herein.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. Communicative coupling of elements may include continuous, periodic, or asynchronous communication among the elements. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as exemplary only and does not describe every possible embodiment, as describing every possible embodiment would be impractical, if not impossible. One could implement numerous alternate embodiments, using either current technology or technology developed after the filing date of this application.

APPENDIX A

Algorithm 1: Salient Frame Selection

1. $F = f_1, f_2, \ldots, f_n$ \\ n is total number of frames
2. $F_h' = f_{1h}', f_{2h}', \ldots, f_{nh}'$
3. $Im = f_1'$ \\using first frame to find crop window size
4. $im_d$ = Denoising(im)
5. $im_e$ = Canny($im_d$) \\extract all edge using canny edge detection
6. lines = houghline ($im_e$) lines = $[l_1, l_2, \ldots, l_h]$
7. [x, y, x', y'] = compute corner points such that crop window contains all lines $l_1, l_2, \ldots, l_h$
8. New-corners = [x, y, x', y']
9. For frame i
10. im-new = crop($f_i'$, New-corners)
11. $[s_1, s_2]$ = size(im-new)
    a. for each $\sigma \in \Sigma = (\sigma_1, \sigma_2, \ldots, \sigma_S)$
        i. for each pixel j $\in$ im-new, j = 1, 2, \ldots, $s_1 \times s_2$
        ii. H = hessian (im-new(j)) \\hessian matrix at pixel j
        iii. $[\lambda_1, \lambda_2] = |H - I\lambda|$ \\$\lambda_1, \lambda_2$ are eigenvalues of H
        iv. $S = \sqrt{\lambda_1^2 + \lambda_2^2}$ \\Frobenus norm of H
        v. $R_B = \dfrac{\lambda_1}{\lambda_2}$ \\ non-similarity measure APPENDIX A-continued $$\text{vi. } V_\sigma(j) = \begin{cases} 0 & \text{if } \lambda_2 < 0 \\ e^{-\frac{R_B^2}{2\beta^2}}\left(1 - e^{-\frac{S^2}{2c^2}}\right) & \text{if } \lambda_2 \geq 0 \end{cases}$$

vii. end for
12. end for
13. End for
  $V(i) = \max_{\sigma_{min} \leq \sigma \leq \sigma_{max}} V\sigma$
14. End for
15. $\max_1 = \text{argmax}_{1 \leq r \leq \frac{n}{2}} \Sigma_i V_r(i)$
16. $\max_2 = \text{argmax}_{1 \leq r \leq \frac{n}{2}, r \neq \max_1} \Sigma_i V_r(i)$
17. $\max_3 = \text{argmax}_{\frac{n}{2} \leq r \leq n} \Sigma_i V_r(i)$
18. $\max_4 = \text{argmax}_{\frac{n}{2} \leq r \leq n, r \neq \max_3} \Sigma_i V_r(i)$
19. $f_{key1} = f_{emax1}$
20. $f_{key2} = f_{emax2}$
21. $f_{key3} = f_{emax3}$
22. $f_{key4} = f_{emax4}$
23. return $F_{key} = (f_{key1}, f_{key2}, f_{key3}, f_{key4})$ Algorithm 2. Denoising 1. $F = f_1, f_2, \ldots, f_n$ \\n is total number of frames
2. For each frame $f_i$
3. $[s_1, s_2] = \text{size}(f_i)$
4. $P = [p_1, p_2, \ldots, p_k]$ \\divide image to k square patches
5. For each pixel $j$, $f_i(j)$, $j = 1, 2, \ldots, s_1 \times s_2$
  a. For each patch $p_k$
  b. $V(k) = \text{gray-intensity}(p_k)$
    i. For each patch $p_i$
    ii. $V(I) = \text{gray-intensity}(p_i)$
    iii. $E(k,l) = ||V(k) - V(l)||_{(2,a)}^2$
    End for
    iv. $Z(j) = \Sigma_j e^{\frac{-E(k,l)}{h^2}}$ \\ degree of filtering
    v. $W(k, l) = \frac{1}{Z(j)} e^{\frac{-E(k,l)}{h^2}}$
    vi. $f'(j) = \Sigma_k w(k, l) V(k)$
    vii. end for
end for
end for
return $F' = (f'_1, f'_2, \ldots, f'_n)$ \\denoised frames Algorithm 3. Vessel Enhancement 1. $F = f_1, f_2, \ldots, f_n$ \\n is total number of frames
2. $F' = \text{Denoising}(f_1, f_2, \ldots, f_n)$
3. For each frame $f'_i \in \mathbb{R}^{s1 \times s2 \times 3}$ \\RGB image
  a. $I_G = f'_i(G)$
  b. $I_R = f'_i(R)$
  c. Art-pixel = $f'_i ((I_R \neq I_G) \text{ and } (I_R == 0))$
  d. Avg = mean $(f'_i)$
  e. For each pixel $p_j \in$ Art − pixel
    i. $N_{p(j)} = 3 \times 3$ neighborhood centered at $p_j$
    ii. If $(\Sigma\Sigma\ Np(j) > 0)$
    iii. $f'_i(j) = \text{mean } (N_{p(j)} \neq 0)$
    iv. else
    v. $f'_i(j) = \text{mean } (f'_i)$
    vi. $f'_{ia} = f'_i$
  End for
  End for
4. $F'_a = (f'_{1a}, f'_{2a}, \ldots, f'_{na})$
5. $F'_{af} = \text{frangi}(F'_a)$
6. $F'_t = ((F'_{af} > 0.1) = 1)$
7. $F'_h = \text{histogram}(F'_t)$
8. Return $F'_h = (f'_{1h}, f'_{2h}, \ldots, f'_{nh})$ Algorithm 4. Vessel Segmentation 1. $F_{key} = (f_{key1}, f_{key2}, f_{key3}, f_{key4})$ \\four salient frames
2. For each frame $f_{keyi}$
  a. O = set of pixels belong to object O in binary image $f_{keyi}$
  b. B = set of pixels belong to back ground of binary image $f_{keyi}$
  c. For each pixel $j \in$ O and pixel $k \in$ B
    i. J = (p,q)
    ii. K = (x, y)
    iii. edt = $\sqrt{(x-p)^2+(y-q)^2}$ \\2-D Euclidean Distance Transform APPENDIX A-continued         iv. $M_1$ = edt(size($f_{keyi}$)) \\contains distance value to the closest back ground pixels
        v. $M_2$ = CI(size($f_{keyi}$))) \\contains the coordinate information of the closest back ground pixels for each pixel of $f_{keyi}$
    End for
        d. For each pixel p ∈ $f_{keyi}$
            i. $b_p$ = closest background pixel to p
            ii. $N_{24}$ = a 5 × 5 neighborhood with center p
            iii. d = $\max_{1,\ldots,24} \|b_p, N_{24}\|$
            iv. $\theta = \max \arccos\left(\frac{\|p,b_p\|^2 + \|p,N_{24}\|^2 - d^2}{2\|p,b_p\|^2\|p,N_{24}\|^2}\right)$
            v. $C = \max_{1,\ldots,24} \frac{graylevel(N_{24})}{graylevel(p)}$
            vi. $p_d$ = pre-defined threshold
            vii. $p_\theta$ = pre-defined threshold
            viii. $p_c$ = EM-GMM($f_{keyi}$) \\computing threshold pd using EM-GMM method
            ix. if (d(p) < $p_d$ and $\theta$ > $p_\theta$ and c(p) > $p_c$)
                p is a pixel level
              Else
                P is a background pixel
    End for
End for
Return $F_s = (f_{s1}, f_{s2}, f_{s3}, f_{s4})$
Algorithm 5. Width Calculation 1. $F_s = (f_{s1}, f_{s2}, f_{s3}, f_{s4})$ \\four salient frames
2. For each pixel p ∈ $f_{si}$
    a. r = distance of any pixel from pixel p
    b. ϵ = increment in r
    c. nd = number of direction of exploration
    d. $\chi = |\{\theta, \theta \in [0, \pi]\}|$
    e. $\bar{\chi} = |\{\bar{\theta}, \bar{\theta} \in [\pi, 2\pi]\}|$
    f. for i = 1 to $\frac{n_d}{2}$
        i. For each $\theta \in \chi$
            1. $p_b$ = boundary point in direction $\theta$ and distance r.
            2. if (p is a $p_b$)
            3. d(i) = r
            4. r = r − ϵ
        ii. For each $\bar{\theta} \in \bar{\chi}$
            1. $p_b$ = boundary point in direction $\bar{\theta}$ and distance r.
            2. if (p is a $p_b$)
            3. $\bar{d}(i) = r$
            4. r = r − ϵ
    end for
    end for
    width(p) = d(i) + $\bar{d}(i)$
    $W_i$ = width(p)
end for
return W = ($W_1, W_2, W_3, W_4$)
Algorithm 6. Artifact and Catheter removing 1. $F_{key} = (f_{key1}, f_{key2}, f_{key3}, f_{key4})$
2. For each frame $f_{keyi}$
    a. $f_n = \frac{I(j, k) \times (w+1)^2}{\sum_{j-w}^{j+w}\sum_{c=k-w}^{c=k+w} I(r, c)}$
    b. h = histogram($f_n$)
    c. $p_1$ = max(h)
    d. $p_2$ = max(h), $p_2 \neq p_1$
    e. threshold = $\frac{p_1 + p_2}{2}$
    f. art-pixels = (($f_n$ < threshold) = 1)
    g. for each pixel p in art-pixels
        i. $N_{50}$ = a 7 × 7 window with center p
        ii. M = mean ($N_{50}$)
        iii. $f_n(P)$ = m
        iv. $f_a = f_n$
        end for
    h. V = ($v_1, v_2, \ldots, v_k$) \\set of end points of skeleton
    i. $S_p = P(v_i, v_j)$ \\shortest path between all pair of end points using Dijekstra Algorithm APPENDIX A-continued j. $\tau = \frac{\sum_{t=i}^{j} f_a(v_t, v_{t+1})}{dist(v_i, v_j)}$ k. cath = max τ
l. $F_c = (f_a \text{ (cath)} = 0)$ \\remove catheter
    End for
End for
Return Fc Algorithm 7. Vessel profile Analysis and Stenosis Detection 1. $F_s = (f_{s1}, f_{s2}, f_{s3}, f_{s4})$
2. For each frame $f_{si}$
3. $T = (t1, t2, \ldots, t_k)$ \\set of all trough computed by water shed analysis
4. For each trough $t_j$
    a. $H_1$ = peak of left side of trough
    b. $H_2$ = peak of right side of trough
    c. d = depth of the trough
    d. W = ((h1 + h2)/2d) × 2/(h1 + h2) × 100
    End for
5. End for

What is claimed:

1. A computer-implemented method for analyzing medical video image data for a subject, the video image data being formed a set of frames of medical image data, the method comprising:
   obtaining, at one or more processors, the medical video image data and performing, at the one or more processors, a pre-processing on the obtained medical video image data by performing on each frame of the video image data
   (i) a denoise filtering on the obtained medical video image data,
   (ii) a removal of a first set of features, and
   (iii) an image quality assessment indicating an amount of usable image data that appears in the frame;
   automatically selecting, at the one or more processors, a subset of the frames of medical image data by performing on each frame of the video image data,
   (i) a vessel segmentation,
   (ii) a histogram analysis after the vessel segmentation, and
   (iii) determining an amount of visible vasculature for each frame, and
   further identifying, at the one or more processors, based on the amount of visible vasculature for each frame, frames having a desired amount of visible vasculature as the subset of frames of medical image data;
   automatically removing, at the one or more processors, artifacts from the subset of frames of medical image data using a shape characteristic machine learning engine trained using a set of artifact training data, wherein the shape characteristic machine learning engine applies a width profile analysis on identified features in the subset of frames to determine if any of the identified features are artifacts, in which case the artifacts are removed;
   automatically performing, at the one or more processors, segmentation on the subset of frames with artifacts removed, wherein the segmentation comprises an extraction of the vasculature of each of the subset of frames;
   automatically performing, at the one or more processors, a width profile analysis on one or more portions of the vasculature in each of the subset of frames to determine an amount of stenosis in the vasculature; and
   aggregating, at the one or more processors, the width profile analyses for the subset of frames to determine of an overall stenosis for the subject.

2. The method of claim 1, wherein performing a pre-processing on the obtained medical video image data comprises performing contrast adjustment on each frame to increase contrast.

3. The method of claim 1, wherein performing a pre-processing on the obtained medical video image data comprises performing the denoise filtering by (i) blocking each pixel and (ii) applying a Gaussian smoothing filter is convolved with each block to reduce the noise.

4. The method of claim 1, wherein performing a pre-processing on the obtained medical video image data comprises performing the denoise filtering by applying a non-local means (NLM) filtering by replacing, for each frame, each pixel of each frame a weighted average pixel intensity of a set of closest nearest pixels, wherein the weighted average pixel intensity is determined from a quadratic pixel distance between the pixel and the set of closest nearest pixels.

5. The method of claim 1, wherein performing a pre-processing on the obtained medical video image data comprises performing a bilinear interpolation on the pixels of each frame.

* * * * *